(12) United States Patent
Herold et al.

(10) Patent No.: US 6,608,569 B2
(45) Date of Patent: Aug. 19, 2003

(54) MULTI-CHANNEL SEGMENTED SLIP RING

(75) Inventors: Mark D. Herold, Stow, OH (US); Theodore A. Resnick, Beachwood, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/977,749

(22) Filed: Oct. 15, 2001

(65) Prior Publication Data

US 2002/0025023 A1 Feb. 28, 2002

Related U.S. Application Data

(62) Division of application No. 09/406,448, filed on Sep. 27, 1999, now Pat. No. 6,327,327.

(51) Int. Cl.[7] .................................................. G08B 1/00
(52) U.S. Cl. ........................ 340/999; 340/686.3; 378/15; 378/98.2
(58) Field of Search .......................... 378/4, 15, 98, 378/98.2; 340/686.3, 672, 286.01, 999

(56) References Cited

U.S. PATENT DOCUMENTS

| | | | |
|---|---|---|---|
| 4,048,503 A | 9/1977 | Taylor | 250/385 |
| 4,242,666 A | 12/1980 | Reschovsky et al. | 340/870.28 |
| 4,404,560 A * | 9/1983 | Williams, Jr. | 340/686.3 X |
| 5,010,254 A | 4/1991 | Moore | 250/551 |
| 5,012,505 A | 4/1991 | Zupancic et al. | 378/130 |
| 5,208,581 A | 5/1993 | Collins | 340/671 |
| 5,220,588 A * | 6/1993 | Deucher et al. | 378/15 |
| 5,336,897 A | 8/1994 | Watanabe et al. | 250/551 |
| 5,469,488 A | 11/1995 | Ono | 378/15 |
| 5,530,424 A | 6/1996 | Harrison et al. | 340/500 |
| 5,577,026 A * | 11/1996 | Gordon et al. | 370/278 |
| 5,579,357 A | 11/1996 | Harrison | 378/4 |
| 5,600,697 A | 2/1997 | Harrison | 378/15 |
| 5,751,837 A | 5/1998 | Watanabe et al. | 382/131 |
| 5,978,438 A * | 11/1999 | Resnick et al. | 378/4 |
| 6,181,766 B1 * | 1/2001 | Pearson, Jr. et al. | 378/15 |
| 6,301,324 B1 * | 10/2001 | Pearson, Jr. et al. | 378/15 |
| 6,327,327 B1 * | 12/2001 | Herold et al. | 378/15 |

FOREIGN PATENT DOCUMENTS

DE 33 31 722 3/1985

* cited by examiner

*Primary Examiner*—Thomas Mullen
(74) *Attorney, Agent, or Firm*—Fay, Sharpe, Fagan, Minnich & McKee, LLP (57) ABSTRACT

A computerized tomography system includes a stationary section (A) and a rotating section electrically linked by at least one interconnecting slip ring (D). On one side the slip ring (D) is configured as a series of electrically conductive segments (20A–20H) separated by non-conductive interruptions (22A–22H). On the other side a like number of transmitters (26A–26H) is in selective electrical contact with the conductive segments (20) depending on a position of the rotating frame. Also included is a de-multiplexer (40) which takes image data from the plurality of receivers (RxA–RxH) and rearranges the image data in a determined sequence. Also shown is an angular encoder (46) for providing angular displacement signals (44) to the de-multiplexer (40) for assistance in reconstructing the data channels (30) in the determined sequence.

18 Claims, 6 Drawing Sheets

MULTI-CHANNEL SEGMENTED SLIP RING

This application is divisional of U.S. application Ser. No. 09/406,448, filed Sep. 27, 1999, now U.S. Pat. No. 6,327,327 B1.

BACKGROUND OF THE INVENTION

The present invention relates to the radiography arts. It finds particular application in conjunction with computerized tomography (CT) scanners and will be described with particular reference thereto. However, it is to be appreciated that the present invention is also amenable to other like applications requiring electrical signal transfer between a moving part and a stationary part.

Heretofore, CT scanners have commonly included a floor mounted frame assembly or gantry which remains stationary during an imaging procedure. A radiation generator, such as an x-ray tube, is mounted to a rotatable frame assembly or section which rotates around a patient being imaged. In third generation scanners, a radiation detector array is located within the rotating frame along with the x-ray tube. It is therefore necessary to provide a mechanism to transfer electrical signals to and from the rotating frame. That is, electrical power and control signals are transferred from the stationary frame to the rotating frame to power and control electronics, hardware, and the x-ray tube.

Additionally, a communications path is provided to transfer imaging data from the radiation detector array in the rotating frame to the stationary frame for image processing. The rotating gantry rotates rapidly, preferably one (1) revolution per second or less. The detector array includes numerous individual detectors, e.g. hundreds or even thousands. The detectors are sampled rapidly, typically in a fraction of a degree of rotation, to a high resolution, e.g. 32 bits or more. The amount of data to be transferred is so massive, that the data transfer rate is becoming a limiting factor in scanner speed and resolution.

Various devices are known for providing the communication path between the rotating frame and the stationary frame. Older CT scanners employed an umbilical cable. Typically, one or more flexible, shielded cables were hardwired to electronics such as the detector array, in the rotating frame. The cables were connected at the other end to stationary side electronics including image processing computers. Unfortunately the umbilical cable is typically capable of +/−360° of rotation. Accordingly, the rotating frame on such umbilical devices is limited to a total of 720° of rotation in one direction before the frame is stopped and rewound in the opposite direction.

Such "cycling" type scanners were good for imaging a small number of slices. For larger volumes, continuous rotating scanners are preferred. The subject moves axially to create a spiral scanning pattern. In continuous rotate third generation systems, slip rings are commonly used to transfer power, data, and control signals. However, continuing improvements keep increasing rates of data transfer. On slip ring data links, the time required to propagate data signals around the circular rings effectively limits the maximum data transfer rate. Signals propagating around the ring in opposite directions may arrive at a reception point at offset times causing interference or garbled reception. Similar limitations are observed in slip ring data links employing capacitance-type data transfer.

Demands for higher data rates are increasingly being met, not through electrical slip ring configurations, but by optical data transmission links. Such data links typically employ a series of pulsating lights distributed around either the stationary frame or the rotating frame. On the opposing frame, an optical receiver is used to detect the synchronously strobing lights. The received light signals are then translated back into electronic image data for follow-on processing. Unfortunately, optical systems are more costly per channel of image data supplied, and greatly depend on the alignment of the optical transmitters and receivers. Moreover, optical systems are unusually sensitive to dirt and/or dust obscuring the optics.

Accordingly, a need exists for yet higher data transfer rates in CT type scanners which provide continuous rotation and reliable high-speed communications.

The present invention contemplates a new and improved method and apparatus for transferring electrical signals which overcomes the above-referenced problems and others.

SUMMARY OF THE INVENTION

In accordance with one aspect of the present invention, a computerized tomography system includes a stationary section defining a central opening and a concentric annular section positioned within the opening. At least one interconnecting data link provides communication between the stationary section and the rotating section. The interconnecting data link includes a plurality of receiving elements spaced angularly around the stationary section. On the rotating section, a plurality of transmitting elements are also angularly spaced. The transmitting elements are equal in number to, and in selective electrical communication with, the plurality of receiving elements.

In accordance with another aspect of the present invention, the plurality of receiving elements includes a ring configured as a plurality of electrically conductive segments separated by non-conductive interruptions.

In accordance with another aspect of the present invention, the transmitters include a number of brushes in selective physical contact with the conductive segments.

In accordance with another aspect of the present invention, the transmitters include capacitive couplers in selective electrical communication with the conductive segments.

In accordance with another aspect of the present invention, the tomography system includes an angular encoder which generates an angular displacement signal corresponding to a relative position of the rotating section within the stationary section. A de-multiplexer is also included which uses data including the angular displacement signal to arrange image data from the plurality of receiving elements into a desired format.

In accordance with another aspect of the present invention, the interconnecting data link further includes a second plurality of receiving elements axially spaced from the first set of receiving elements. On the rotating section, a second plurality of transmitting elements is likewise axially spaced from the first plurality of transmitting elements.

In accordance with another aspect of the present invention, the second plurality of receiving elements are angularly offset from the first plurality of receiving elements such that electrical communication between the stationary section and the rotating section is continuously provided.

In accordance with another embodiment of the present invention, a diagnostic imaging machine includes a rotating frame housing at least one array of radiation detectors selectively outputting imaging signals. A stationary frame is provided to support the rotating frame, and a plurality of simultaneous communication paths are provided for electrically transferring the imaging signals from the rotating frame to the stationary frame.

In accordance with another aspect of the present invention, the plurality of communication paths includes a ring configured as a plurality of electrically conductive segments separated by non-conductive interruptions. Further, a plurality of transmitting elements are in electrical communication with at least a portion of the radiation detectors, and in electrical communication with exactly one of the conductive segments when the rotating frame is at selected rotational angles.

In accordance with another aspect of the present invention, a rotational position sensor provides an angular displacement signal corresponding to the rotational angle of the rotating frame. A multi-channel decoder reorders data from each receiver into data channels based on the angular displacement signal provided.

In accordance with another aspect of the present invention, the imaging machine further includes at least a second slip ring parallel to the first slip ring also having a plurality of electrically conductive segments separated by non-conductive interruptions.

In accordance with another aspect of the present invention, the electrically conductive segments of the second slip ring are offset angularly from the segments of the first slip ring.

In accordance with another embodiment of the present invention, a radiographic process includes, while rotating an x-ray tube and an x-ray detector around an examination region, selectively activating the x-ray tube to direct radiation through the examination region onto the x-ray detector. Responsive to the radiation detected by the x-ray detector, channels of image data are generated. Selected ones of the image channels are then simultaneously electrically transmitted over a moving interface.

In accordance with another aspect of the present invention, following the transmitting, each of the selected plurality of data channels is arranged into a defined format.

In accordance with another aspect of the present invention, based on the detection of rotation, the transmitting is periodically interrupted.

One advantage of the present invention is that it improves data transfer efficiency.

Another advantage of the present invention resides in its simplicity.

Another advantage of the present invention resides in its extremely high data transfer rates.

Yet another advantage of the present invention resides in its space efficiency. Fewer slip ring assemblies can carry more data.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not be construed as limiting the invention.

DETAILED DESCRIPTION OF THE PREFERRED EMBODIMENTS

Figure 1:
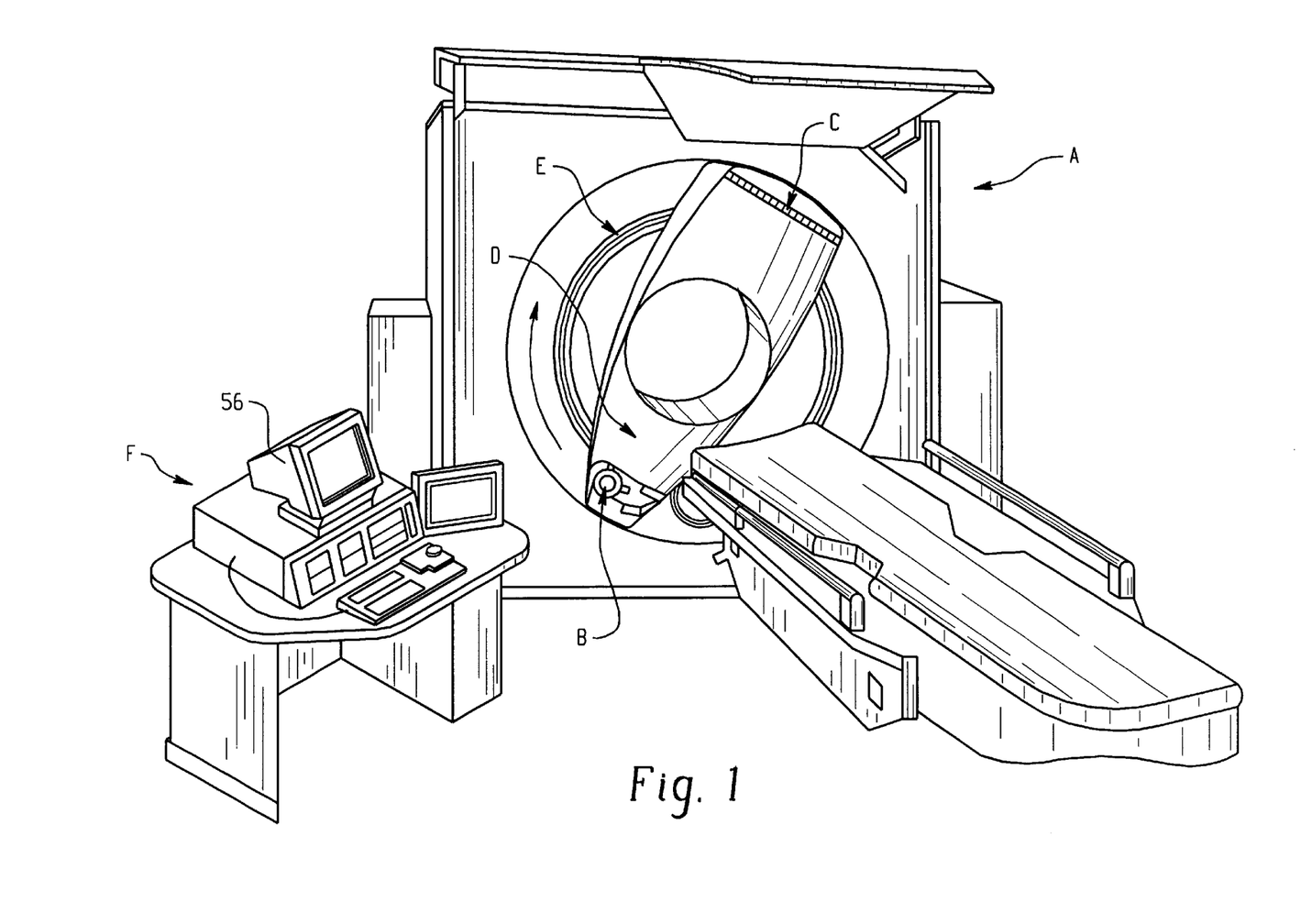
FIG. 1 is a diagrammatic illustration of a CT scanner in accordance with the present invention.

With reference to FIG. 1, a CT scanner includes a floor mounted stationary frame portion or section A whose position remains fixed during data collection. An x-ray tube B and x-ray detector array C are mounted on a rotating frame or section D disposed within the stationary frame A. A multi-channel segmented slip ring E is disposed between the stationary frame A and the rotating frame D to provide electrical communication between the frames.

Figure 2A:
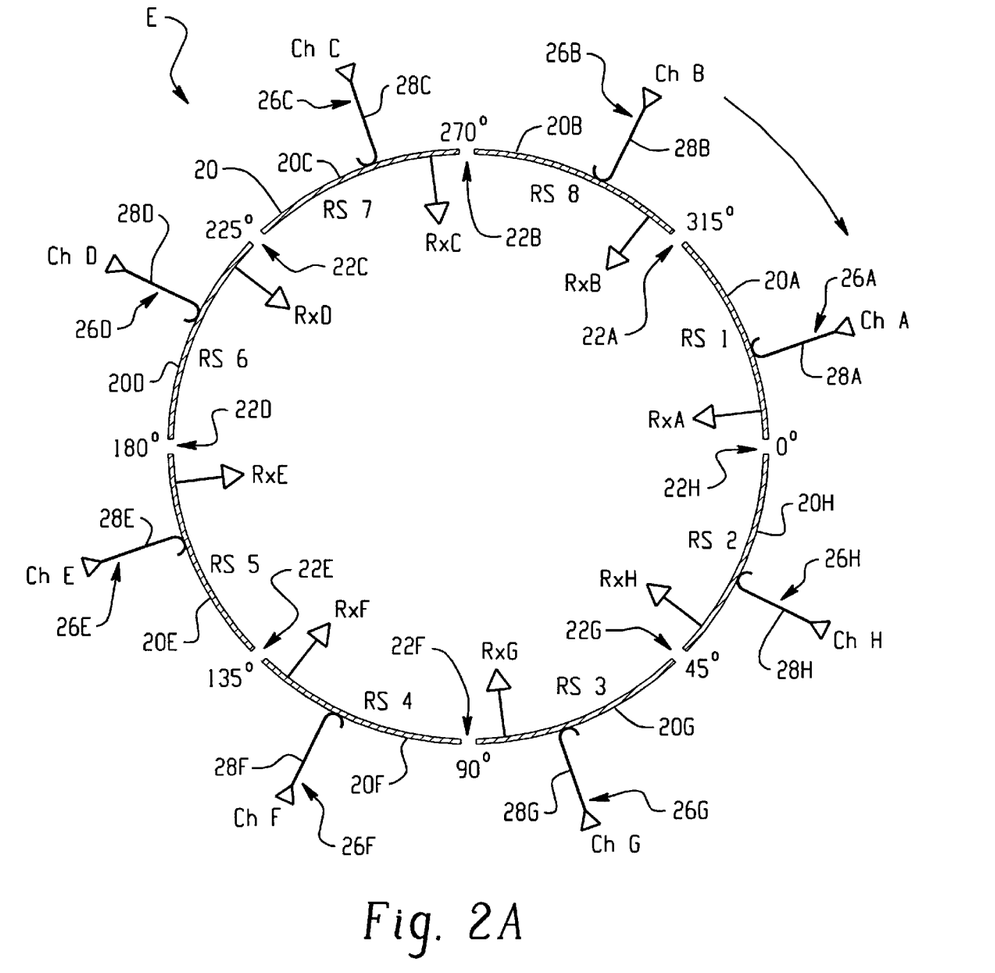
FIGS. 2A and 2B are exemplary illustrations of single multi-channel segmented slip rings according to the present invention.

With reference now to FIG. 2A, the segmented slip ring E includes a plurality of electrically conductive segments 20A–20H configured as a ring. The segments 20 are separated by a like number of non-conductive interruptions 22A–22H. Those skilled in the art will appreciate that the segments 20 can be disposed either on the rotating frame or the stationary frame with no loss of functionality. In the illustrated embodiment, receiving circuitry RxA-RxH is electrically connected to each conductive segment 20 for filtering and amplifying the signal as is known in the art. Additionally, the receiving circuits RxA-RxH route the signal to a de-multiplexer more fully discussed below.

The segmented slip ring E also includes a plurality of transmitting elements 26A–26H each in electrical communication with at least a portion of the radiation detector C (FIG. 1). As illustrated in FIG. 2, the transmitting elements include a brush 28A–28H with at least an electrically conductive tip. As used herein the term 'brush' is understood to refer to any of a single wire, a spring biased electrical element, a group of wires in close physical proximity, or the like. As above, those skilled in the art will recognize that the transmitting elements 26 can be positioned on either the stationary frame or the rotating frame with no loss of functionality. Moreover, artisans will appreciate that a ground path is provided between the stationary frame and the rotating frame via means known in the art such as a dedicated non-segmented slip ring and the like.

Figure 2B:
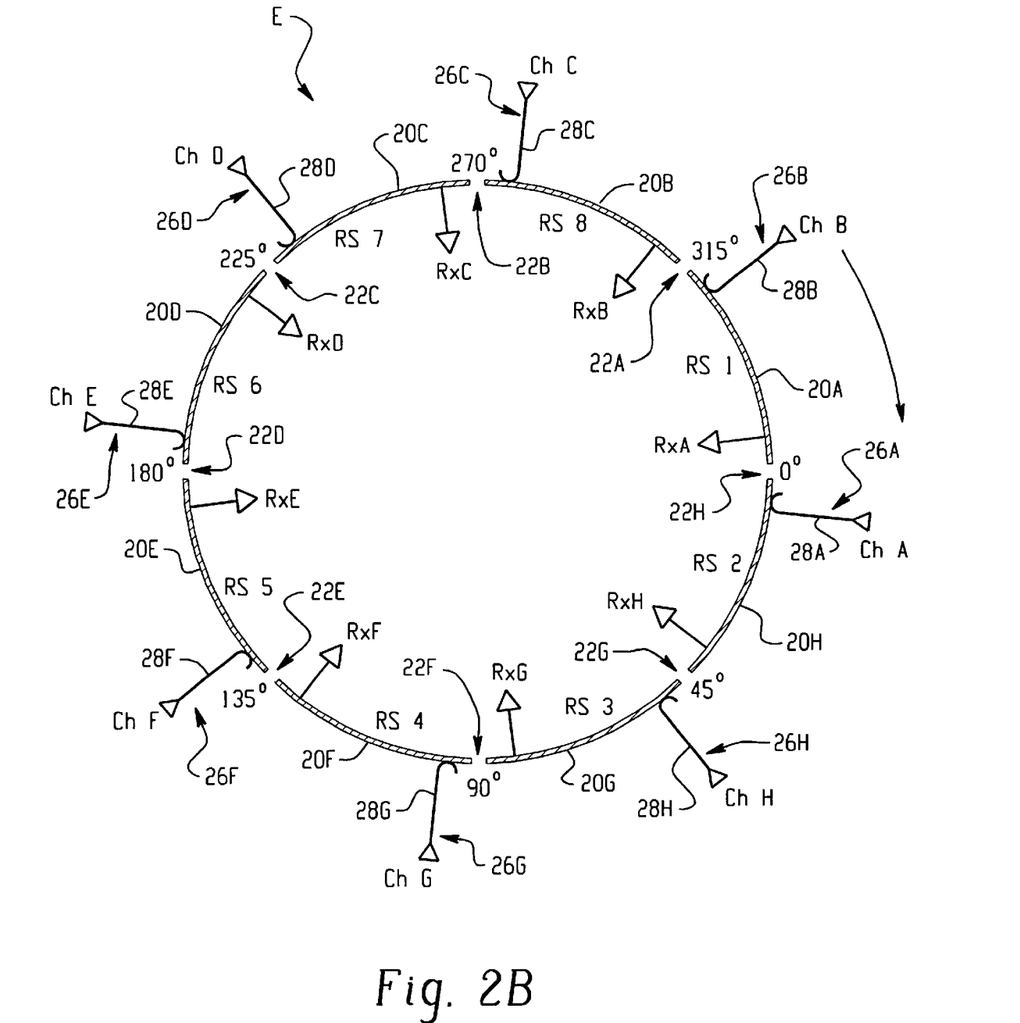

As is apparent now from combined reference to FIGS. 2A and 2B, as the rotating frame moves or is angularly offset, the brushes 28 move over the conductive segments 20 uniformly until reaching the non-conductive interruptions 22. In other words, when the rotating frame is positioned such that the transmitter 26 and the brushes 28 are in contact with a conductive segment 20, electrical communication is established between the rotating frame D and the stationary frame A. Those skilled in the art can appreciate that dividing the slip ring into a plurality of conductive segments can be seen as effecting a parallel format data transfer. For example, in the illustrated embodiment eight data streams may be transmitted simultaneously one between each brush and conductive segment pair. Additionally, those skilled in the art will appreciate that use of the relatively short conductive segments desirably reduces time delay and/or phase errors within the signals conducted.

Referring now to FIG. 2B, when the rotating frame urges the brushes through a non-conductive interruption 22 onto a following conductive segment 20, it can now be appreciated that each transmitter 26 is in electrical communication with a different receiver 24. For example, in FIG. 2A transmitter 26H is in electrical contact with receiver RxH. FIG. 2B illustrates a slight angular displacement of the rotating frame which has the effect of placing transmitter 26H in electrical communication with receiver RxG. Thus, as the rotating frame rotates, each transmitter 26 must periodically cease sending data as the brushes approach the non-conductive interruptions 22. Moreover, positioning information accompanies the data from the receivers Rx to ensure correct processing and association with the originating transmitter. In other words, imaging signals from transmitter 26A are transmitted to the stationary frame A cyclically first through receiver RxA, then through receiver RxH, then RxG, etc.

Figure 3:
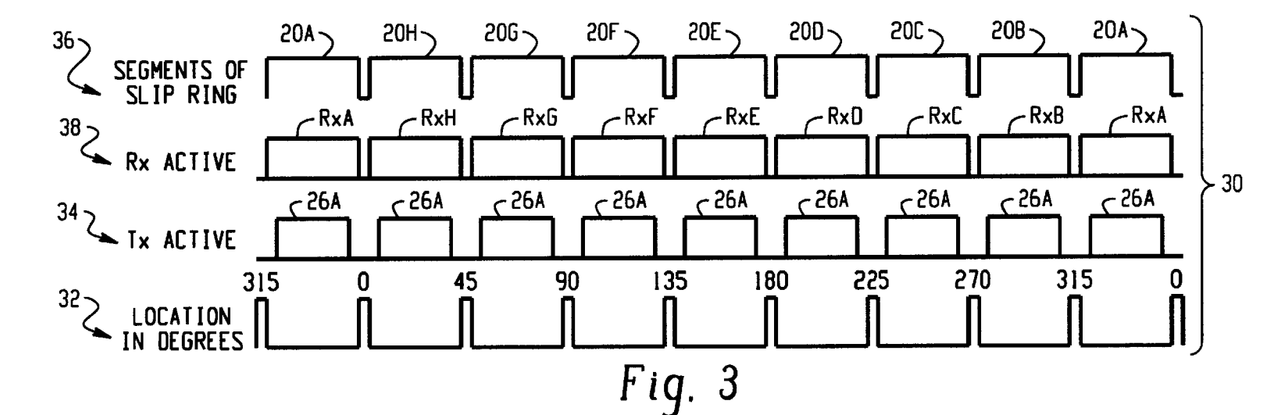
FIG. 3 is a time line showing usage of segments, receivers, transmitters, and relative angular locations.

In order to best appreciate the timing required to preferably control transmit sequences to occur only when the transmitters are in electrical communication with the receivers best illustrated by reference to FIG. 3. Information about the relative rotational angle of the rotating frame is preferably provided to both transmitters 26 and receivers Rx. The angular location is graphically depicted on timing graph 30 by the location axis 32. Those skilled in the art will appreciate that by gating the transmission and/or the reception of data on and off as the brushes pass through the non-conductive interruptions 22, data loss and data garble are minimized. In order to gate the transmitters and receivers on and off, the data illustrated on the location axis 32, that is the location of the rotating ring, is preferably provided to both the portion of the slip ring assembly on the rotating frame, and the portion of the slip ring located on the stationary frame. In fact, regardless of the source of the rotational or angular information, a path such as a non-segmented slip ring section or the like is provided to communicate the angular information. It can be appreciated that the channel A data, as seen on the transmit axis 34 sequences through each segment 20 of the segmented slip ring, as illustrated by the segments axis 36 to receivers associated with each segment. The receivers illustrated by the receiver axis 38 route the signals for further processing on the stationary side of the gantry.

Those skilled in the art will appreciate that gating individual transmitters and receivers on and off depending on the relative rotational position of the rotating section may be required in certain embodiments, for example single rings or dual aligned rings comprising one signal pair. In other embodiments however, continuous data streams are also envisioned across a multiplicity of concentric parallel slip ring pairs angularly offset from one another. In other words, as the brushes approach gaps on a first slip ring, the transmitting and receiving responsibility for each particular channel may be switched to a second parallel slip ring where the brushes are in communication with the slip ring segments. In an additional embodiment, a single segmented slip ring may provide a signal pair to insure against sporadic signal loss. Such an embodiment is envisioned as dedicating two receivers and two transmitter on each segmented slip ring to any particular channel. In other words the eight segmented slip ring illustrated in FIG. 2 would be capable of channels A–D in duplicate as opposed to a singular path for channels A–H as illustrated. Yet another potential embodiment includes different numbers of brushes and ring segments angularly staggered within one slip ring's assembly. In such a configuration, angular position or rotational information is preferably still provided to both the rotating segment and the stationary segment. The angular offset of brushes and segments will ensure that a number of brush/segment pairs are always in electrical communication. it is now apparent at a variety of configurations of slip ring assemblies, segments within an assembly and brushes within an assembly are possible depending on the particular system requirements needed.

Figure 4:
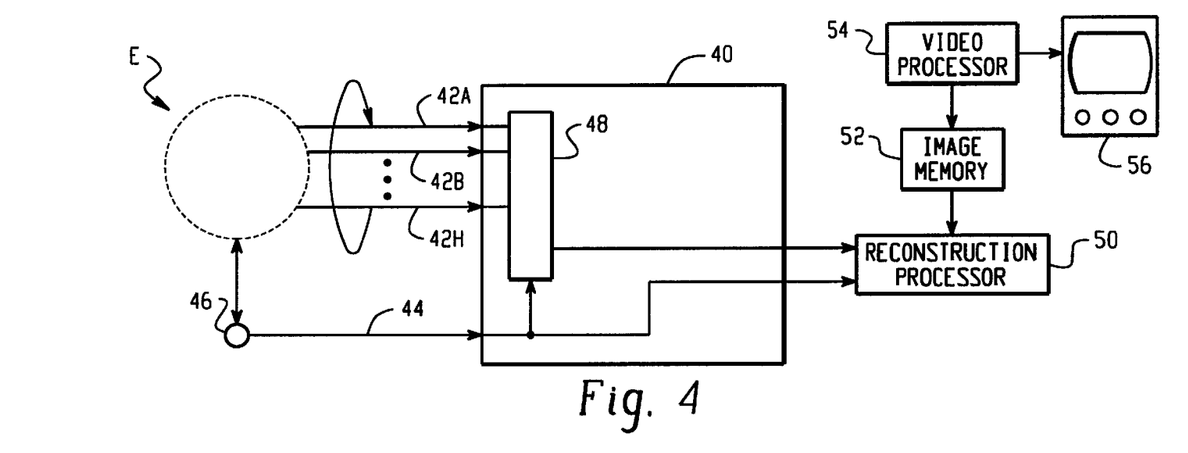
FIG. 4 is an illustration of an angular encoder and image data formatting device in accordance with the present invention.

Referring now to FIG. 4, a de-multiplexer or decoder 40 preferably receives image data 42A–42H from the plurality of receivers Rx in addition to an angular displacement signal 44 from an angular encoder 46. The de-multiplexer or decoder 40 preferably includes a register 48 controlled by angular displacement signal 44 which reorders data from each of the receivers Rx into a channelized coherent data stream for further processing by an image reconstruction computer F (FIG. 1). It should be appreciated that de-multiplexer 40 simultaneously reorders receiver data for each channel depending on the relative position sensed by encoder 46. In parallel processing reconstruction systems, each detector of the array C is connected with one of the transmitters on the rotating frame. The demultiplexer outputs the signal from each detector, in parallel to a parallel reconstruction processor.

In either single or parallel channel systems, a reconstruction processor 50 reconstructs the image data into an electronic image representation that is stored in a memory 52. A video processor 54 converts selected portions of the electronic image representation into slice images, three-dimensional renderings, projection images, or the like which images are displayed on a human readable monitor 56.

Figure 5:
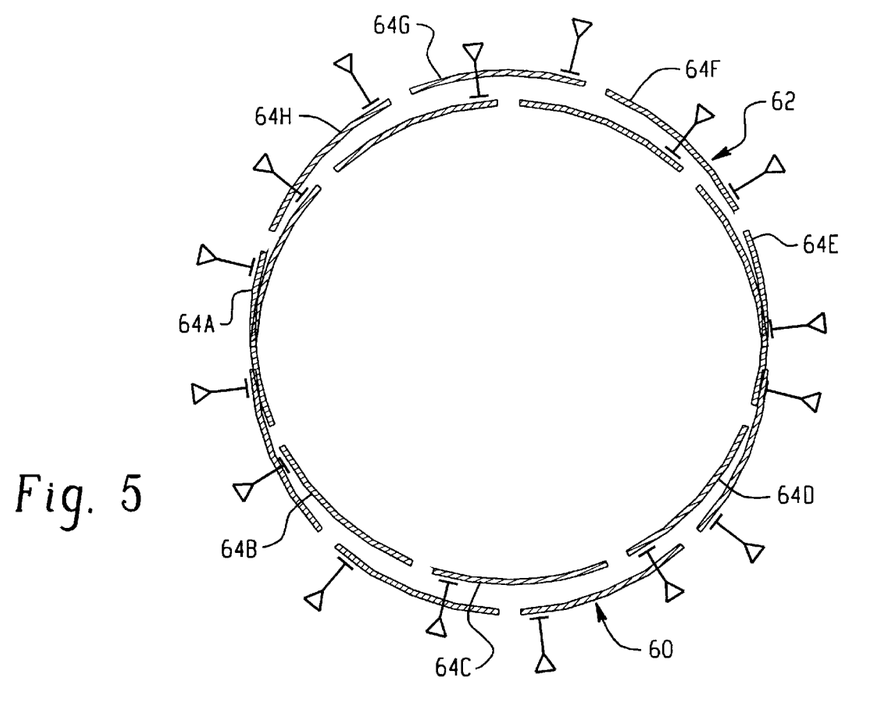
FIG. 5 is an illustrative diagram of two segmented slip rings angularly offset from one another.

Referring now to FIG. 5, an alternate embodiment of a multi-channel segmented slip ring includes a first slip ring 60 similar in most respects to the segmented slip ring of FIG. 2. In the embodiment illustrated by FIG. 5 however, a capacitive transmitting system is used as opposed to the brush system previously discussed. Such capacitive electrical communication is known in the electrical arts. In addition, a second segmented slip ring is included 62 which includes segments 64 angularly offset from the segments of the first ring 60. In other words, one of the slip rings 60, 62 will provide electrical communication between the stationary side and the rotating side at all times. This redundancy can be used for error correction or to increase the data rate over the slip ring. Those skilled in the art will appreciate that a similar angularly offset multi-ring configuration is workable in the brush system discussed above.

Figure 6:
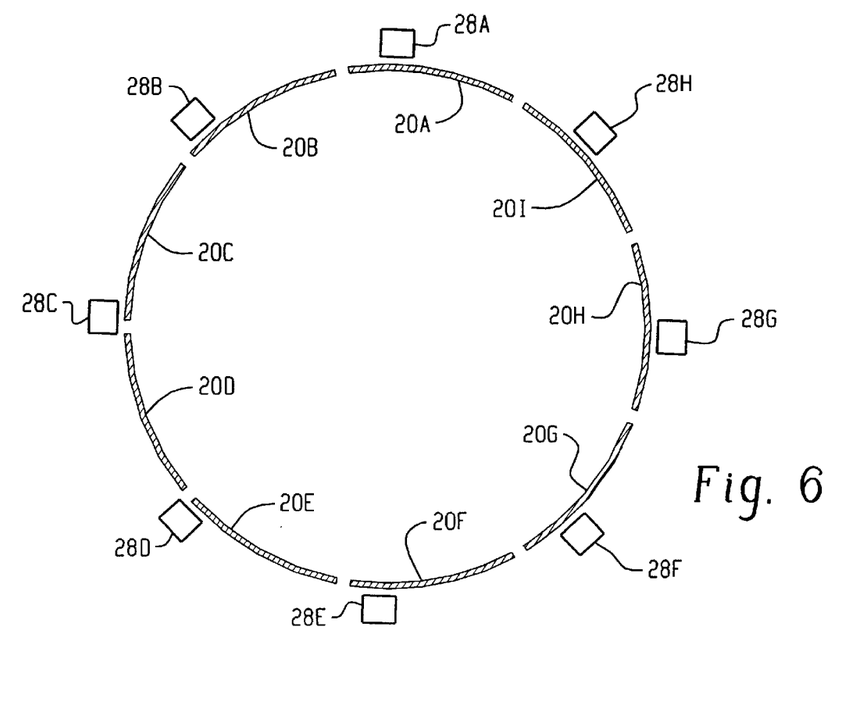
FIG. 6 is an illustrative diagram of an alternate embodiment of the present invention.

With reference to FIG. 6, in another alternate embodiment, the slip ring has N segments 20, where N is a plural integer, preferably odd. N−1 brushes 28 contact the segments. In this manner, no two brushes are in the non-conductive interruptions at the same time. By connecting each detector with 2 brushes (and programming the demultiplexer 40 accordingly), a continuous data stream is provided from each detector.

Figure 7:
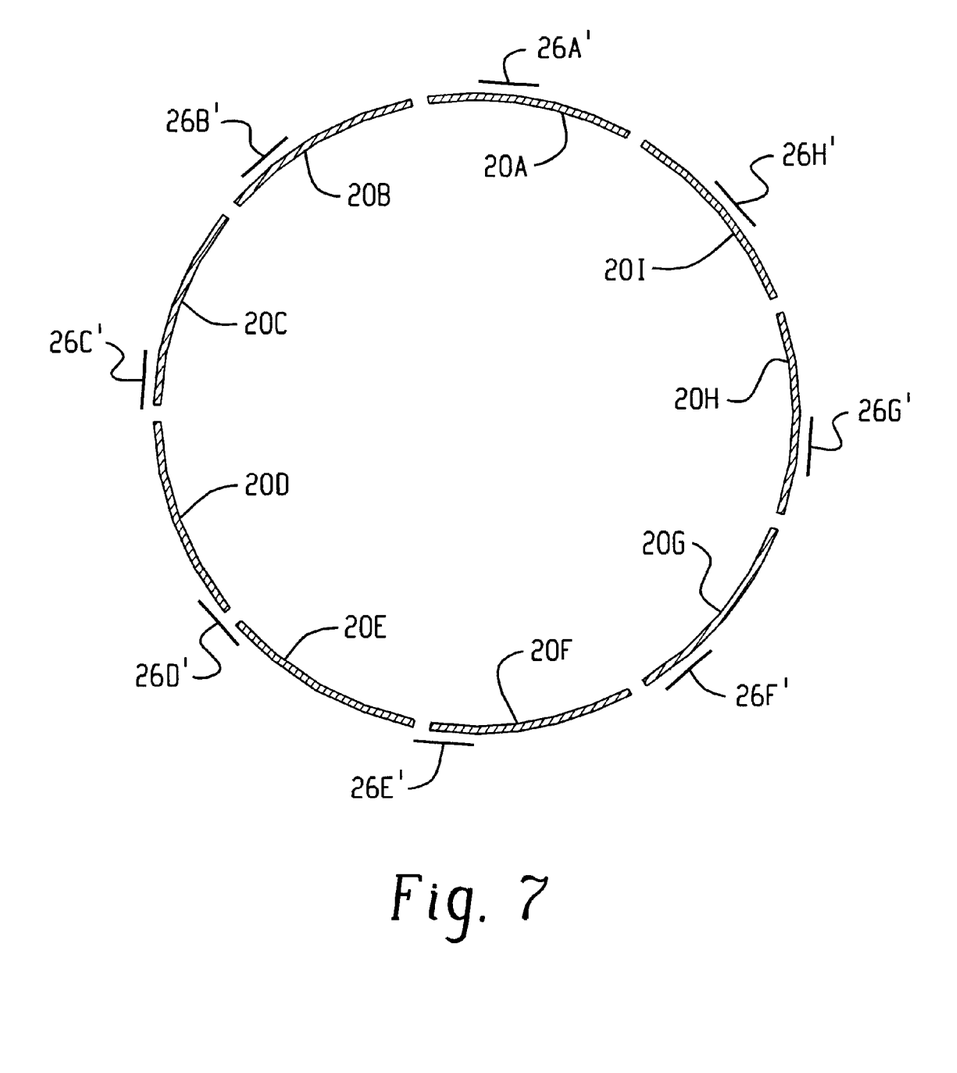
FIG. 7 is an illustrative diagram of another alternate embodiment of the present invention.

In another alternate embodiment there are again N ring segments 20 and N−1 transmitters 26'. Each transmitter 26' has a brush, brush set, or capacitive element which is large enough to span the non-conductive interruption between segments 20. The brushes, brush sets, or capacitive elements are spaced from each other by more than the arc of the ring segments. Partially overlapping segments, as illustrated in FIG. 7, facilitate making communication with two adjacent rings.

The invention has been described with reference to the preferred embodiments. Obviously, modifications and alterations will occur to others upon reading and understanding the preceding detailed description, such as changing the number of conductive segments, providing for a spare conductive segment/transmitter pair, or application of the principles herein disclosed to other areas such as industrial process control, aerospace application or medical instrumentation. it is intended that the invention be construed as including all such modifications and alterations insofar as they come within the scope of the appended claims or the equivalents thereof.

Having thus described the preferred embodiments, the invention is now claimed to be:

1. A data transfer method comprising:
   generating relative rotational movement between a first ring of electrically conductive segments and a plurality of electrically conductive brushes;
   applying a plurality of data streams, one to each electrically conductive brush; and
   at selected rotational angles, establishing physical contact between at least selected brushes and ring segments to receive the plurality of data streams, one on each segment of the ring.

2. The data transfer method as set forth in claim 1, further including:
   monitoring the relative rotational movement.

3. A data transfer method comprising:
   generating relative rotational movement between a first ring of electrically conductive segments and a plurality of signal communication elements;
   monitoring the relative rotational movement;
   applying a plurality of data streams, one to each signal communication element;
   at selected rotational angles, receiving the plurality of data streams, one on each segment of the ring; and
   sorting each of the plurality of data streams in accordance with the monitored relative rotational movement.

4. The data transfer method as set forth in claim 3, wherein the plurality of signal communication elements include capacitive couplers, the receiving step including:
   capacitively coupling at least selected signal communication elements and ring segments.

5. The data transfer method as set forth in claim 3, further including:
   generating relative rotational movement between a second ring of electrically conductive segments and a plurality of signal communication elements.

6. An interconnecting data link which transmits data between two sections mounted for relative rotation, said interconnecting data link comprising:
   at least one ring including a plurality of elongated electrically conductive arc segments separated by short non-conductive interruptions spaced angularly around one of said sections, the elongated electrically conductive arc segments being much longer than the short non-conductive interruptions; and,
   a plurality of signal communication elements spaced angularly around the other of said sections, the plurality of signal communication elements in selective electrical communication with said plurality of electrically conductive ring segments.

7. The interconnecting data link as set forth in claim 6 wherein the plurality of arc segments are unequal in number with the plurality of signal communication elements.

8. An interconnecting data link which transmits data between two sections mounted for relative rotation, said interconnecting data link comprising:
   at least one ring including a plurality of electrically conductive arc segments separated by non-conductive interruptions spaced angularly around one of said sections;
   a plurality of signal communication elements spaced angularly around the other of said sections, the plurality of signal communication elements in selective electrical communication with said plurality of electrically conductive ring segments, the signal communication elements including one of:
      brushes in selective physical contact with the electrically conductive ring segments; and,
      capacitive couplers spaced from the conductive segments.

9. An interconnecting data link which transmits data between two sections mounted for relative rotation, said interconnecting data link comprising:
   at least one ring including a plurality of electrically conductive arc segments separated by non-conductive interruptions spaced angularly around one of said sections;
   a plurality of signal communication elements spaced angularly around the other of said sections, the plurality of signal communication elements being in selective electrical communication with said plurality of electrically conductive ring segments;
   an encoder which generates an angular displacement signal indicative of the relative rotation of the sections; and
   a de-multiplexer which receives the angular displacement signal and the data, and sorts the data in accordance with the angular displacement signals.

10. An interconnecting data link which transmits data between two sections mounted for relative rotation, said interconnecting data link comprising:
    a first ring including a first plurality of electrically conductive arc segments separated by non-conductive interruptions spaced angularly around one of said sections;
    a second ring including a second plurality of electrically conductive arc segments axially spaced from said first plurality of conductive segments;
    a first plurality of signal communication elements spaced angularly around the other of said sections, the first plurality of signal communication elements in selective electrical communication with said first plurality of electrically conductive ring segments; and,
    a second plurality of electrical communication elements in electrical communication with the second ring.

11. The interconnecting data link as set forth in claim 10, wherein the second plurality of electrical communication elements are equal in number to, and in selective electrical communication with, said second plurality of electrically conductive segments.

12. The interconnecting data link as set forth in claim 10, wherein one of the first electrically conductive segments and the first electrical communication elements are angularly displaced from the second electrically conductive segments and the second electrical communication elements.

13. A multi-channel slip ring assembly comprising:
    a plurality of electrically conductive arc segments disposed end to end around a first circular ring with non-conductive interruptions therebetween;

a plurality of electrical signal transfer elements disposed in a spaced relationship around a second circular ring, the first and second rings being concentric about a common axis with the arc segments and the transfer elements in electrical communication with each other, the arc segments and the transfer elements being mounted to undergo relative rotation around the common axis;

a rotational position sensor for measuring the relative rotation;

a means for applying electrical signals to one of the arc segments and the transfer elements;

a means for retrieving the electrical signals from the other of the arc segments and the transfer elements; and, a multi-channel decoder connected with the angular encoder and at least one of the arc segments and the transfer elements.

14. The slip ring assembly as set forth in claim 13 wherein the arc segments each span a first common arc and the transfer elements are separated by a second circumferential distance.

15. The slip ring assembly as set forth in claim 14 wherein the first common arc is different from the second circumferential distance.

16. A slip ring assembly comprising:

a first plurality of electrically conductive arc segments disposed end to end around a first circular ring with non-conductive interruptions therebetween;

a second plurality of electrically conductive arc segments disposed end to end around the first circular ring adjacent and axially displaced from the first plurality of arc segments;

a first plurality of electrical signal transfer elements disposed in a spaced relationship around a second circular ring, the first and second rings being concentric about a common axis with the first arc segments and the first transfer elements in electrical communication with each other, the first arc segments and the first transfer elements being mounted to undergo relative rotation around the common axis;

a second plurality of electrical signal transfer elements disposed in a spaced relationship around the second circular ring in electrical communication with the second arc segments.

17. The slip ring assembly as set forth in claim 16 wherein at least one of:

the second arc segments are circumferentially displaced from the first arc segments;

the second transfer elements are circumferentially displaced from the first transfer elements.

18. A multi-channel segmented slip ring assembly comprising:

a plurality of electrically conductive arc segments disposed end to end around a first circular ring with non-conductive interruptions therebetween;

a plurality of electrical signal transfer elements disposed in a spaced relationship around a second circular ring, the transfer elements include at least one of:

brushes; and, capacitive couplers;

the first and second rings being concentric about a common axis with the arc segments and the transfer elements in electrical communication with each other, the arc segments and the transfer elements being mounted to undergo relative rotation around the common axis.

* * * * *